US010519085B2

(12) United States Patent
Himmler et al.

(10) Patent No.: US 10,519,085 B2
(45) Date of Patent: Dec. 31, 2019

(54) PROCESS FOR PREPARING SUBSTITUTED 2-ARYLETHANOLS

(71) Applicant: BAYER CROPSCIENCE AKTIENGESELLSCHAFT, Monheim am Rhein (DE)

(72) Inventors: Thomas Himmler, Odenthal (DE); Peter Brüchner, Krefeld (DE)

(73) Assignee: BAYER CROPSCIENCE AKTIENGESELLSCHAFT, Monheim am Rhein (DE)

( * ) Notice: Subject to any disclaimer, the term of this patent is extended or adjusted under 35 U.S.C. 154(b) by 0 days.

(21) Appl. No.: 16/070,244

(22) PCT Filed: Jan. 9, 2017

(86) PCT No.: PCT/EP2017/050325
§ 371 (c)(1),
(2) Date: Jul. 13, 2018

(87) PCT Pub. No.: WO2017/121699
PCT Pub. Date: Jul. 20, 2017

(65) Prior Publication Data
US 2019/0023633 A1 Jan. 24, 2019

(30) Foreign Application Priority Data
Jan. 15, 2016 (EP) .................... 16151430

(51) Int. Cl.
C07C 29/36 (2006.01)
C07C 33/20 (2006.01)
C07C 33/46 (2006.01)
C07C 43/23 (2006.01)

(52) U.S. Cl.
CPC ............ C07C 29/36 (2013.01); C07C 33/20 (2013.01); C07C 33/46 (2013.01); C07C 43/23 (2013.01)

(58) Field of Classification Search
CPC ......... C07C 43/23; C07C 29/36; C07C 33/46; C07C 33/20
See application file for complete search history.

(56) References Cited

U.S. PATENT DOCUMENTS 2,058,373 A * 10/1936 Weissenborn .......... C07C 29/00
260/665 G

FOREIGN PATENT DOCUMENTS

| EP | 456063 A2 | 11/1991 |
|---|---|---|
| EP | 521334 A1 | 1/1993 |
| EP | 596298 A2 | 5/1994 |
| EP | 613884 A2 | 9/1994 |
| EP | 613885 A2 | 9/1994 |
| EP | 668267 A1 | 8/1995 |
| WO | 95/001971 A1 | 1/1995 |
| WO | 95/020572 A1 | 8/1995 |
| WO | 95/026954 A1 | 10/1995 |
| WO | 96/025395 A1 | 8/1996 |
| WO | 96/035664 A1 | 11/1996 |
| WO | 97/001535 A1 | 1/1997 |
| WO | 97/002243 A1 | 1/1997 |
| WO | 97/036868 A1 | 10/1997 |
| WO | 97/043275 A2 | 11/1997 |
| WO | 98/005638 A2 | 2/1998 |
| WO | 98/006721 A1 | 2/1998 |
| WO | 98/025928 A1 | 6/1998 |
| WO | 99/024437 A1 | 5/1999 |
| WO | 99/043649 A1 | 9/1999 |
| WO | 99/048869 A1 | 9/1999 |
| WO | 99/055673 A1 | 11/1999 |
| WO | 01/17972 A2 | 3/2001 |
| WO | 01/23354 A2 | 4/2001 |
| WO | 01/74770 A1 | 10/2001 |
| WO | 03/013249 A1 | 2/2003 |
| WO | 03/062244 A1 | 7/2003 |
| WO | 2004/007448 A1 | 1/2004 |
| WO | 2004/024688 A1 | 3/2004 |
| WO | 04/065366 A1 | 8/2004 |
| WO | 04/080962 A1 | 9/2004 |
| WO | 04/111042 A1 | 12/2004 |
| WO | 05/044791 A2 | 5/2005 |
| WO | 05/044796 A1 | 5/2005 |
| WO | 05/048710 A1 | 6/2005 |
| WO | 05/049569 A1 | 6/2005 |
| WO | 05/066125 A1 | 7/2005 |
| WO | 05/092897 A2 | 10/2005 |
| WO | 06/000355 A1 | 1/2006 |
| WO | 06/029799 A1 | 3/2006 |
| WO | 06/056281 A1 | 6/2006 |
| WO | 06/056282 A1 | 6/2006 |
| WO | 06/089633 A2 | 8/2006 |
| WO | 07/048545 A2 | 5/2007 |

(Continued)

OTHER PUBLICATIONS

Ma, Wuping et al., "Synthesis of New Four-Atom-Linked Capped Porphyrins", Journal of Organic Chemistry, 1995, pp. 8081-8083, vol. 60.
Boudjouk, Philip et al., "The Synthesis of 1-Silaphenalanes from 1,8-difunctional Naphthalenes. Confirmation of the Structures of the Pyrolysis Products of (1-Naphthyl)vinyldichlorosilane", Journal of Organometallic Chemistry, 1981, pp. 33-45, vol. 221.
Bost, John J. et al., "Effect of Structural Changes on Adsorption of Certain Alcohol 3,5-dinitrobenzoates on Silicic Acid", Journal of Organic Chemistry, Jan. 1957, pp. 51-55, vol. 22.

(Continued)

Primary Examiner — Rosalynd A Keys
(74) Attorney, Agent, or Firm — McBee Moore Woodward & Vanik IP, LLC

(57) ABSTRACT

The invention relates to a process for preparing substituted 2-arylethanols of the formula (I) by reacting Grignard compounds of the formula (II) in the presence of a copper compound with ethylene oxide. Moreover, the invention relates to novel substituted 2-arylethanols of the formula (I).

10 Claims, No Drawings

(56) References Cited

FOREIGN PATENT DOCUMENTS

| | | |
|---|---|---|
| WO | 07/073856 A2 | 7/2007 |
| WO | 07/096058 A1 | 8/2007 |
| WO | 07/121868 A1 | 11/2007 |
| WO | 07/140881 A1 | 12/2007 |
| WO | 08/067873 A1 | 6/2008 |
| WO | 08/067910 A | 6/2008 |
| WO | 08/067911 A1 | 6/2008 |
| WO | 08/138551 A2 | 11/2008 |
| WO | 09/015801 A1 | 2/2009 |
| WO | 09/039975 A1 | 4/2009 |
| WO | 09/049851 A1 | 4/2009 |
| WO | 09/115262 A1 | 9/2009 |
| WO | 10/052161 A2 | 5/2010 |
| WO | 10/063378 A1 | 6/2010 |
| WO | 10/063670 A1 | 6/2010 |
| WO | 10/102758 A2 | 9/2010 |
| WO | 11/067135 A1 | 6/2011 |
| WO | 11/067240 A1 | 6/2011 |
| WO | 11/098440 A2 | 8/2011 |
| WO | 11/098443 A1 | 8/2011 |
| WO | 11/123937 A1 | 10/2011 |
| WO | 2012/110519 A1 | 8/2012 |
| WO | 2013/080896 A1 | 6/2013 |

OTHER PUBLICATIONS

Sheridan, H. et al., "Synthesis and antispasmodic activity of nature identical substituted indanes and analogues", European Journal of Medical Chemistry, 1990, pp. 603-608, vol. 25.

Zeng, Mingshuo et al., "A Highly Active and Air-Stable Ruthenium Complex for the Ambient Temperature Anti-Markovnikov Reductive Hydration of Terminal Alkynes", Journal of the American Chemical Society, 2014, pp. 7058-7067, vol. 136.

Huynh, Chanh, "Copper-Catalysed Reactions of Grignard Reagents with Epoxides and Oxetane", Tetrahedron Letters, 1979, pp. 1503-1506, No. 17.

Normant, J.F. et al., "Condensation des Reactifs de Grignard Sur Les Halohydrines Libres ou Bloquees en Presence de Quantites Catalytiques de Cu (I)", Tetrahedron Letters, 1977, pp. 3263-3266, No. 37, Pergamon Press, Great Britain.

Linstrumelle, Gerard et al., "Copper-Catalysed Reactions of Allylic Grignard Reagents with Epoxides", Tetrahedron Letters, 1978, pp. 4069-4072, No. 42, Pergamon Press, Great Britain.

Schüpbach, Björn et al., "A divergent synthesis of oligoarylalkanethiols with Lewis-basic N-donor termini", Organic & Biomolecular Chemistry, 2010, pp. 3552-3562, vol. 8.

International Search Report of International Patent Application No. PCT/EP2017/050325 dated Feb. 10, 2017.

\* cited by examiner

PROCESS FOR PREPARING SUBSTITUTED 2-ARYLETHANOLS

CROSS-REFERENCE TO RELATED APPLICATIONS

This application is a National Stage entry of International Application No. PCT/EP2017/050325, filed 9 Jan. 2017, which claims priority to European Patent Application No. 16151430.2, filed 15 Jan. 2016.

BACKGROUND

Field

The present invention relates to a process for preparing substituted 2-arylethanols, and to novel substituted 2-arylethanols.

Description of Related Art

Substituted 2-arylethanols are important intermediates for the manufacture of bioactive compounds which can be used specifically for controlling pests in crop protection. In particular, they serve for the manufacture of insecticidal, acaricidal or herbicidal cyclic ketoenols (for example EP-A-456 063, EP-A-521 334, EP-A-596 298, EP-A-613 884, EP-A-613 885, WO 95/01 971, WO 95/26 954, WO 95/20 572, EP-A-0 668 267, WO 96/25 395, WO 96/35 664, WO 97/01 535, WO 97/02 243, WO 97/36 868, WO 97/43275, WO 98/05638, WO 98/06721, WO 98/25928, WO 99/24437, WO 99/43649, WO 99/48869, WO 99/55673, WO 01/17972, WO 01/23354, WO 01/74770, WO 03/013249, WO 03/062244, WO 04/007448, WO 04/024 688, WO 04/065366, WO 04/080962, WO 04/111042, WO 05/044791, WO 05/044796, WO 05/048710, WO 05/049569, WO 05/066125, WO 05/092897, WO 06/000355, WO 06/029799, WO 06/056281, WO 06/056282, WO 06/089633, WO 07/048545, WO 07/073856, WO 07/096058, WO 07/121868, WO 07/140881, WO 08/067873, WO 08/067910, WO 08/067911, WO 08/138551, WO 09/015801, WO 09/039975, WO 09/049851, WO 09/115262, WO 10/052161, WO 10/102758, WO 10/063378, WO 10/063670, WO 10/102758, WO 11/098443, WO 11/098440, WO 11/067135, WO 11/067240, WO 12/110519), where the substituted 2-arylethanols can be used to prepare the required substituted phenylacetic acids (WO 2013/080896).

A large number of methods for preparing substituted 2-arylethanols has already become known. One method often found in the literature consists in reducing substituted phenylacetic acid esters with a complex hydride such as, for example, lithium aluminium hydride (see for example WO 2011/123937). Thus, the starting materials used here are precisely those compounds which can often only be obtained by complex methods and which should be easier to obtain direct from the substituted 2-arylethanols.

Furthermore, it is known to react a haloaromatic with acetylene or a mono-protected acetylene such as for example trimethylsilylacetylene or 2-methylbut-3-yn-2-ol in a Sonogashira reaction with palladium catalysis to give the corresponding protected arylacetylene, to remove the protective group and then to subject the alkyne function to an anti-Markovnikov addition of water, for example catalyzed by ruthenium complexes (*J. Amer. Chem. Soc.* 136 (2014) 7058-67). This method has the disadvantage of involving two transition-metal-catalysed steps, one of which uses the very expensive metal palladium.

A further known method consists in metallating a haloaromatic with butyllithium and then reacting it with ethylene oxide (see for example *Eur. J. Med. Chem.* 25 (1990) 603-8). This process has the disadvantage that the metallation with butyllithium generally has to be carried out at very low temperatures, for example −78° C., which can be realized industrially only in a complex and expensive manner and thus renders the process uneconomical.

A further known method consists in reacting a haloaromatic with magnesium to give the corresponding Grignard compound and then allowing this Grignard compound to react with ethylene oxide to give the substituted 2-arylethanol. This method has the disadvantage that under certain circumstances a mixture of the desired substituted 2-arylethanol and undesired substituted 1-arylethanol is obtained (see comparative experiments), as a result of which complex purification operations are necessary and the yield is unsatisfactory.

Although it has already been described that the rate of the reaction of Grignard compounds with oxiranes, including ethylene oxide, can be increased by adding copper compounds such as copper iodide (see for example *Tetrahedron Letters* 1978, 4069-72; *Tetrahedron Letters* 1979, 1503-6; *Org. Biomol. Chem.* 2010, 3552-62), there has hitherto been no indication made known that the selectivity can also be improved in the desired way.

It is likewise known that 2-arylethanols are obtained by reacting an aryl-Grignard compound with 2-bromoethanol, likewise in the presence of a catalytic amount of copper(I) bromide (*Tetrahedron Letters* 1977, 3263-66). In this connection, it is very disadvantageous that the Grignard compound is used in a very high excess of 3 mol equivalents, as a result of which this process becomes uneconomical.

Accordingly, there continues to be a high requirement for an improved process for preparing substituted 2-arylethanols.

SUMMARY

It has now been found that in the reaction of Grignard compounds with ethylene oxide the formation of undesired 1-arylethanols can surprisingly be suppressed by adding catalytic amounts of copper salts.

The present invention therefore involves a novel process for preparing substituted 2-arylethanols of the formula (I)

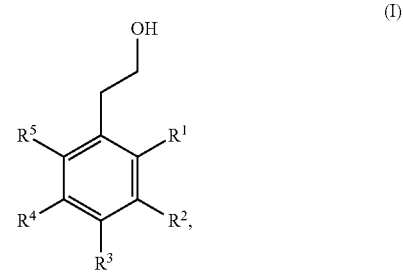

in which $R^1$, $R^5$ independently of one another represent $C_1$-$C_6$-alkyl, $C_1$-$C_6$-fluoroalkyl having 1 to 13 fluorine atoms, optionally substituted $C_6$-$C_{10}$-aryl, fluorine, chlorine, a radical $NR^6_2$, $OR^6$ or $SR^6$, where $R^6$ represents $C_1$-$C_6$-alkyl, $C_1$-$C_2$-fluoroalkyl having 1 to 5 fluorine atoms or phenyl, $R^2$, $R^3$, $R^4$ independently of one another represent hydrogen, $C_1$-$C_6$-alkyl, $C_1$-$C_6$-fluoroalkyl having 1 to 13 fluorine atoms, optionally substituted $C_6$-$C_{10}$-aryl, fluorine, chlorine, a radical $NR^6{}_2$, $OR^6$ or $SR^6$, where $R^6$ represents $C_1$-$C_6$-alkyl, $C_1$-$C_2$-fluoroalkyl having 1 to 5 fluorine atoms or phenyl, characterized in that a Grignard compound of the formula (II)

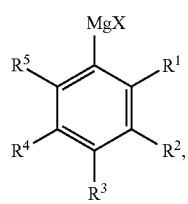

in which the radicals $R^1$ to $R^5$ have the meanings given above and

X represents chlorine, bromine or iodine (preferably bromine or iodine, particularly preferably bromine), is reacted in the presence of a copper compound with ethylene oxide.

DETAILED DESCRIPTION OF A PREFERRED EMBODIMENT

The compound of the formula (II) is also intended to include the other forms of the Schlenk equilibrium known to the person skilled in the art, with and without complexation of solvent molecules.

Preference is given to the preparation of 2-arylethanols of the formula (I) in which $R^1$, $R^5$ independently of one another represent $C_1$-$C_6$-alkyl, $C_1$-$C_6$-fluoroalkyl having 1 to 13 fluorine atoms, optionally substituted $C_6$-$C_{10}$-aryl, fluorine, chlorine, a radical $NR^6{}_2$, $OR^6$ or $SR^6$, where $R^6$ represents $C_1$-$C_6$-alkyl, $C_1$-$C_2$-fluoroalkyl having 1 to 5 fluorine atoms or phenyl, $R^2$, $R^3$, $R^4$ independently of one another represent hydrogen, $C_1$-$C_6$-alkyl, $C_1$-$C_2$-fluoroalkyl having 1 to 5 fluorine atoms, phenyl optionally substituted by $C_1$-$C_4$-alkyl, $C_1$-$C_4$-alkoxy, fluorine or chlorine, fluorine, chlorine or a radical $OR^6$, where $R^6$ represents $C_1$-$C_6$-alkyl, $C_1$-$C_2$-fluoroalkyl having 1 to 5 fluorine atoms or phenyl.

Particular preference is given to the preparation of 2-arylethanols of the formula (I) in which $R^1$, $R^5$ independently of one another represent methyl, ethyl, n-propyl, iso-propyl, trifluoromethyl, phenyl optionally substituted by methyl, ethyl, n-propyl, iso-propyl, methoxy, ethoxy or fluorine, fluorine, chlorine or a radical $OR^6$, where $R^6$ represents methyl, ethyl, n-propyl, iso-propyl, n-butyl, tert-butyl, $CHF_2$, $CF_3$ or $C_2F_5$ and $R^2$, $R^3$, $R^4$ independently of one another represent hydrogen, methyl, ethyl, n-propyl, iso-propyl, trifluoromethyl, phenyl optionally substituted by methyl, ethyl, n-propyl, iso-propyl, methoxy, ethoxy or fluorine, fluorine, chlorine or a radical $OR^6$, where $R^6$ represents methyl, ethyl, n-propyl, iso-propyl, n-butyl, tert-butyl, $CHF_2$, $CF_3$ or $C_2F_5$.

Very particular preference is given to the preparation of the following 2-arylethanols:

2-(4-chloro-2,6-dimethylphenyl)ethanol
2-(4-chloro-2,6-diethylphenyl)ethanol
2-(2,6-dimethyl-4-trifluoromethylphenyl)ethanol
2-(4-fluoro-2,6-dimethylphenyl)ethanol
2-(2,6-dimethyl-4-trifluoromethoxyphenyl)ethanol
2-(2-ethyl-4,6-dimethylphenyl)ethanol
2-(2,4-diethyl-6-methylphenyl)ethanol
2-(3-chloro-2,6-dimethylphenyl)ethanol.

Emphasis is given to the preparation of 2-(4-chloro-2,6-dimethylphenyl)ethanol.

The above-listed general radical definitions and elucidations or those listed in preferred ranges may be combined arbitrarily with one another, in other words including combinations between the respective ranges and preferred ranges. They apply both to the end products and correspondingly to the intermediates.

The preparation of the Grignard compounds of the formula (II) takes place by generally known methods of organic chemistry from the corresponding substituted aryl halide and magnesium. The aryl halides that can be used here are the chloro-, bromo- or iodoaromatics. Preference is given to using the bromo- and iodoaromatics, particularly preferably the bromoaromatics.

Suitable solvents for the preparation of the Grignard compounds of the formula (II) are for example open-chain and cyclic ethers such as, for example, diethyl ether, methyl tertiary-butyl ether, tertiary-amyl methyl ether, tetrahydrofuran, 2-methyltetrahydrofuran, 2,5-dimethyltetrahydrofuran, methyl cyclopentyl ether or 1,4-dioxane; aromatic hydrocarbons such as toluene, xylenes or mesitylene; mixtures of these solvents. Preference is given to working in cyclic ethers or in mixtures of cyclic ethers with aromatic hydrocarbons.

The temperature during the preparation of the Grignard compounds of the formula (II) can vary within wide limits. Preference is given to working at between 20° C. and 100° C.

The magnesium is generally used in an excess based on the haloaromatics, usually 1.05 to 1.2 equivalents.

After the reaction of the haloaromatic with the magnesium has taken place, the not fully reacted excess magnesium can be removed by a filtration.

In the inventive step of the process, the Grignard compound of the formula (II) prepared as described above is reacted in the presence of a copper compound with ethylene oxide.

Suitable solvents for the inventive step of the process are the solvents that are used for the preparation of the Grignard compound of the formula (II): Open-chain and cyclic ethers such as diethyl ether, methyl tertiary-butyl ether, tertiary-amyl methyl ether, tetrahydrofuran, 2-methyltetrahydrofuran, 2,5-dimethyltetrahydrofuran, methyl cyclopentyl ether or 1,4-dioxane; aromatic hydrocarbons such as toluene, xylenes or mesitylene; mixtures of these solvents. Preference is given to working in cyclic ethers or in mixtures of cyclic ethers with aromatic hydrocarbons. Particular preference is given to tetrahydrofuran, 2-methyltetrahydrofuran, methyl cyclopentyl ether, mixtures of these ethers and mixtures of these ethers with toluene.

The copper compounds used in the inventive step of the process are copper(I) or copper(II) compounds. By way of example, mention may be made of copper(I) iodide, copper(I) bromide, copper(I) chloride, copper(I) oxide, copper(II) bromide, copper(II) chloride, copper(II) oxide, copper(II) sulphate, copper(II) nitrate, copper(II) acetate. Preference is given to using copper(I) iodide, copper(I) bromide, copper (II) bromide and copper(I) chloride, particularly preferably copper(I) iodide, copper(I) bromide and copper(II) bromide.

The amount of copper compound in the inventive step of the process can be varied within wide limits. Preference is given to using the smallest amount of copper compound necessary to bring about the desired effect. Preference is given to using 0.1 to 50 mol percent, based on the Grignard compound of the formula (II); particularly preferably 0.5 to 15 mol percent.

The amount of ethylene oxide in the inventive step of the process can likewise be varied within wide limits. Preference is given to using between 0.9 and 3 mol equivalents of ethylene oxide, based on the Grignard compound of the formula (II). Particular preference is given to using between 1 and 2 mol equivalents of ethylene oxide.

The ethylene oxide can either be introduced as a gas into the solution of the Grignard compound of the formula (II), or the ethylene oxide is metered in as a solution. Suitable solvents here are preferably those solvents that have been used in the preparation of the Grignard compound of the formula (II).

The reaction temperature in the inventive step of the process is between −30 and +100° C. Preferably, it is between 0 and 80° C., particularly preferably between +10 and +50° C.

The reaction in the inventive step of the process can in principle also be carried out under reduced or increased pressure. Preference is given to working at atmospheric pressure.

The work-up of the reaction mixtures takes place by customary and known methods of organic chemistry.

The present invention likewise provides novel substituted 2-arylethanols of the formula (I)

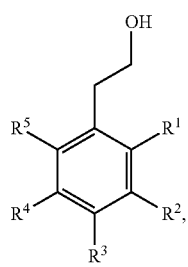

in which the radicals $R^1$, $R^2$, $R^3$, $R^4$, $R^5$ have the meanings given in Table 1.

TABLE 1

| Compound | $R^1$ | $R^2$ | $R^3$ | $R^4$ | $R^5$ |
|---|---|---|---|---|---|
| I-1 | Me | H | Cl | H | Me |
| I-2 | Me | H | Cl | H | Et |
| I-3 | Et | H | Cl | H | Et |
| I-4 | Me | H | Cl | H | n-Pr |
| I-5 | Et | H | Cl | H | n-Pr |
| I-6 | n-Pr | H | Cl | H | n-Pr |
| I-7 | Me | H | Cl | H | iso-Pr |
| I-8 | Et | H | Cl | H | iso-Pr |
| I-9 | iso-Pr | H | Cl | H | iso-Pr |
| I-10 | iso-Pr | H | Cl | H | n-Pr |
| I-11 | Me | H | F | H | Me |
| I-12 | Me | H | F | H | Et |
| I-13 | Et | H | F | H | Et |
| I-14 | Me | H | $CF_3$ | H | Me |
| I-15 | Me | H | $CF_3$ | H | Et |
| I-16 | Et | H | $CF_3$ | H | Et |

TABLE 1-continued

| Compound | $R^1$ | $R^2$ | $R^3$ | $R^4$ | $R^5$ |
|---|---|---|---|---|---|
| I-17 | Me | H | $OCF_3$ | H | Me |
| I-18 | Me | H | Me | H | Et |
| I-19 | Me | H | Et | H | Et |
| I-20 | Me | H | Et | H | Me |
| I-21 | Me | Cl | H | H | Me |
| I-22 | Et | Cl | H | H | Me |
| I-23 | Et | H | H | Cl | Me |

Me = Methyl,
Et = Ethyl,
n-Pr = n-Propyl,
iso-Pr = iso-Propyl

Particular preference is given to novel substituted 2-arylethanols of the formula (I) in which the radicals $R^1$, $R^2$, $R^3$, $R^4$, $R^5$ have the meanings given in Table 2.

TABLE 2

| Compound | $R^1$ | $R^2$ | $R^3$ | $R^4$ | $R^5$ |
|---|---|---|---|---|---|
| I-1 | Me | H | Cl | H | Me |
| I-2 | Me | H | Cl | H | Et |
| I-3 | Et | H | Cl | H | Et |
| I-4 | Me | H | Cl | H | n-Pr |
| I-5 | Et | H | Cl | H | n-Pr |
| I-6 | n-Pr | H | Cl | H | n-Pr |
| I-11 | Me | H | F | H | Me |
| I-12 | Me | H | F | H | Et |
| I-13 | Et | H | F | H | Et |
| I-18 | Me | H | Me | H | Et |
| I-19 | Me | H | Et | H | Et |
| I-20 | Me | H | Et | H | Me |
| I-21 | Me | Cl | H | H | Me |
| I-22 | Et | Cl | H | H | Me |
| I-23 | Et | H | H | Cl | Me |

Very particular preference is given to novel substituted 2-arylethanols of the formula (I) in which the radicals $R^1$, $R^2$, $R^3$, $R^4$, $R^5$ have the meanings given in Table 3.

TABLE 3

| Compound | $R^1$ | $R^2$ | $R^3$ | $R^4$ | $R^5$ |
|---|---|---|---|---|---|
| I-1 | Me | H | Cl | H | Me |
| I-2 | Me | H | Cl | H | Et |
| I-3 | Et | H | Cl | H | Et |
| I-11 | Me | H | F | H | Me |
| I-12 | Me | H | F | H | Et |
| I-13 | Et | H | F | H | Et |
| I-18 | Me | H | Me | H | Et |
| I-19 | Me | H | Et | H | Et |
| I-20 | Me | H | Et | H | Me |
| I-21 | Me | Cl | H | H | Me |

Over and above this, preference is given to the following compound:

2-(4-chloro-2,6-dimethylphenyl)ethanol (compound I-1).

The oxidation of the substituted 2-arylethanols of the formula (I) to the substituted phenylacetic acids required as building blocks for example for insecticidal or herbicidal cyclic ketoenols can take place by methods of organic chemistry known in principle. By way of example, mention may be made of the oxidation with potassium permanganate or the Zhao-Anelli oxidation with 2,2,6,6-tetramethylpiperidinyloxyl, sodium hypochlorite and sodium chlorite (Organic Syntheses, 81, 195-203; 2005).

The present invention will be illustrated in more detail by the examples below, without any intention of limiting it thereto.

EXAMPLES

Example 1: 2-(4-Chloro-2,6-dimethylphenyl)ethanol (Compound I-1)

To a solution of bromo(4-chloro-2,6-dimethylphenyl) magnesium, prepared at 30-35° C. from 50 mmol of 4-chloro-2,6-dimethylbromobenzene, 1 mmol of bromo(4-chloro-2,6-dimethylphenyl)magnesium (to start the Grignard synthesis) and 55.5 mmol of magnesium in 50 ml of tetrahydrofuran, were added 5 mmol of copper(I) iodide. Then, 48 ml of a 2.5-3.3 molar solution of ethylene oxide in tetrahydrofuran (120 mmol, calculated for a concentration of 2.5 M) were metered in at 20° C. over the course of 30 minutes. After 16 hours at 20° C., the reaction mixture was placed on 100 g of ice and adjusted to pH 1 with sulphuric acid. After triple extraction with in each case 50 ml of methylene chloride, the combined organic phases were extracted once by shaking with 30 ml of water, dried over magnesium sulphate and concentrated on a rotary evaporator. There remained an oil, in which, according to GC/MS analysis, the ratio of 2-(4-chloro-2,6-dimethylphenyl)ethanol to 1-(4-chloro-2,6-dimethylphenyl)ethanol was >99:1.

GC/MS: m/e=184 ($M^+$ ($^{35}Cl$), 25%), 153 ($^{35}Cl$, 100%).

$^1$H-NMR (600 MHz, d-DSMO): δ=2.28 (s, 6H), 2.75 (m, 2H), 3.45 (m, 2H), 4.74 (m, 1H), 7.0 (s, 2H) ppm.

Example 2: 2-(4-Chloro-2,6-dimethylphenyl)ethanol (Compound I-1)

To a solution of bromo(4-chloro-2,6-dimethylphenyl) magnesium, prepared at 30-35° C. from 10 mmol of 4-chloro-2,6-dimethylbromobenzene, 1 mmol of bromo(4-chloro-2,6-dimethylphenyl)magnesium (to start the Grignard synthesis) and 11.1 mmol of magnesium in 10 ml of tetrahydrofuran, were added 0.1 mmol of copper(I) iodide. Then, 9.6 ml of a 2.5-3.3 molar solution of ethylene oxide in tetrahydrofuran (24 mmol, calculated for a concentration of 2.5 M) were metered in at 20° C. over the course of 30 minutes. After 16 hours at 20° C., the reaction mixture was placed on 100 g of ice and adjusted to pH 1 with sulphuric acid. After triple extraction with in each case 50 ml of methylene chloride, the combined organic phases were extracted once by shaking with 30 ml of water, dried over magnesium sulphate and concentrated on a rotary evaporator. There remained an oil, in which, according to GC/MS analysis, the ratio of 2-(4-chloro-2,6-dimethylphenyl)ethanol to 1-(4-chloro-2,6-dimethylphenyl)ethanol was >99:1.

Example 3: 2-(4-Chloro-2,6-dimethylphenyl)ethanol (Compound I-1)

To a solution of bromo(4-chloro-2,6-dimethylphenyl) magnesium, prepared at 30-35° C. from 10 mmol of 4-chloro-2,6-dimethylbromobenzene, 1 mmol of bromo(4-chloro-2,6-dimethylphenyl)magnesium (to start the Grignard synthesis) and 11.1 mmol of magnesium in 10 ml of tetrahydrofuran, were added 1 mmol of copper(I) iodide. Then, 9.6 ml of a 2.5-3.3 molar solution of ethylene oxide in tetrahydrofuran (24 mmol, calculated for a concentration of 2.5 M) were metered in at 50° C. over the course of 30 minutes. After 16 hours at 50° C., the reaction mixture was placed on 100 g of ice and adjusted to pH 1 with sulphuric acid. After triple extraction with in each case 50 ml of methylene chloride, the combined organic phases were extracted once by shaking with 30 ml of water, dried over magnesium sulphate and concentrated on a rotary evaporator. There remained an oil, in which, according to GC/MS analysis, the ratio of 2-(4-chloro-2,6-dimethylphenyl)ethanol to 1-(4-chloro-2,6-dimethylphenyl)ethanol was >99:1.

Comparative Example 1: 2-(4-Chloro-2,6-dimethylphenyl)ethanol

To a solution of bromo(4-chloro-2,6-dimethylphenyl) magnesium, prepared at 30-50° C. from 10 mmol of 4-chloro-2,6-dimethylbromobenzene and 11.1 mmol of magnesium in 10 ml of tetrahydrofuran, were metered in 8.8 ml of a 2.5-3.3 molar solution of ethylene oxide in tetrahydrofuran (22 mmol, calculated for a concentration of 2.5 M) at 50° C. over the course of 30 minutes. After 3 hours at 50° C., the reaction mixture was placed on 100 g of ice and adjusted to pH 1 with sulphuric acid. After triple extraction with in each case 50 ml of methylene chloride, the combined organic phases were extracted once by shaking with 30 ml of water, dried over magnesium sulphate and concentrated on a rotary evaporator. There remained an oil, in which, according to GC/MS analysis, the ratio of 2-(4-chloro-2,6-dimethylphenyl)ethanol to 1-(4-chloro-2,6-dimethylphenyl)ethanol was 87:13.

Comparative Example 2: 2-(4-Chloro-2,6-dimethylphenyl)ethanol

To a solution of bromo(4-chloro-2,6-dimethylphenyl) magnesium, prepared at 30-35° C. from 10 mmol of 4-chloro-2,6-dimethylbromobenzene, 1 mmol of bromo(4-chloro-2,6-dimethylphenyl)magnesium (to start the Grignard synthesis) and 11.1 mmol of magnesium in 10 ml of tetrahydrofuran, were metered in 9.6 ml of a 2.5-3.3 molar solution of ethylene oxide in tetrahydrofuran (24 mmol, calculated for a concentration of 2.5 M) at 50° C. over the course of 30 minutes. After 16 hours at 50° C., the reaction mixture was placed on 100 g of ice and adjusted to pH 1 with sulphuric acid. After triple extraction with in each case 50 ml of methylene chloride, the combined organic phases were extracted once by shaking with 30 ml of water, dried over magnesium sulphate and concentrated on a rotary evaporator. There remained an oil, in which, according to GC/MS analysis, the ratio of 2-(4-chloro-2,6-dimethylphenyl)ethanol to 1-(4-chloro-2,6-dimethylphenyl)ethanol was 78:22.

Example 4: 2-(4-Chloro-2,6-dimethylphenyl)ethanol (Compound I-1)

To a solution of 20 mmol of bromo(4-chloro-2,6-dimethylphenyl)magnesium in 20 ml tetrahydrofuran were added 2 mmol of copper(I) bromide. Then, 16 ml of a 2.5-3.3 molar solution of ethylene oxide in tetrahydrofuran (40 mmol, calculated for a concentration of 2.5 M) were metered in at 20° C. over the course of 30 minutes. After 16 hours at 20° C., the reaction mixture was placed on 100 g of ice and adjusted to pH 1 with sulphuric acid. After triple extraction with in each case 50 ml of methylene chloride, the combined organic phases were extracted once by shaking with 30 ml of water, dried over magnesium sulphate and concentrated on a rotary evaporator. There remained an oil, in which, according to GC/MS analysis, the ratio of 2-(4-chloro-2,6-dimethylphenyl)ethanol to 1-(4-chloro-2,6-dimethylphenyl)ethanol was >99:1.

Example 5: 2-(4-Chloro-2,6-dimethylphenyl)ethanol (Compound I-1)

The procedure was as in Example 4 but now using 1 mmol of copper(II) bromide instead of Cu(I)Br. The ratio of 2-(4-chloro-2,6-dimethylphenyl)ethanol to 1-(4-chloro-2,6-dimethylphenyl)ethanol was >99:1.

Example 6: 2-(4-Chloro-2,6-dimethylphenyl)ethanol (Compound I-1)

The procedure was as in Example 4 but now using 1 mmol of copper(I) chloride instead of Cu(I)Br. The ratio of 2-(4-chloro-2,6-dimethylphenyl)ethanol to 1-(4-chloro-2,6-dimethylphenyl)ethanol was >99:1.

Example 7: 2-(2,6-Dimethylphenyl)ethanol

To a solution of 2,6-dimethylphenylmagnesium, prepared at 30-35° C. from 20 mmol of 2,6-dimethylbromobenzene and 22.2 mmol of magnesium in 10 ml of tetrahydrofuran, were added 0.2 mmol of copper(I) iodide. Then, 8.8 ml of a 2.5-3.3 molar solution of ethylene oxide in tetrahydrofuran (22 mmol, calculated for a concentration of 2.5 M) were metered in at 20° C. over the course of 30 minutes. After 16 hours at 20° C., the reaction mixture was placed on 100 g of ice and adjusted to pH 1 with sulphuric acid. After triple extraction with in each case 50 ml of methylene chloride, the combined organic phases were extracted once by shaking with 30 ml of water, dried over magnesium sulphate and concentrated on a rotary evaporator. There remained an oil, in which, according to GC/MS analysis, the ratio of 2-(2,6-dimethylphenyl)ethanol to 1-(2,6-dimethylphenyl)ethanol was 97.5:2.5.

Comparative Example 3:
2-(2,6-Dimethylphenyl)ethanol

Into a solution of 2,6-dimethylphenylmagnesium, prepared at 40-55° C., towards the end for a few minutes at 65° C., from 200 mmol of 2,6-dimethylbromobenzene and 222 mmol of magnesium in 100 ml of tetrahydrofuran, were introduced 215 mmol of ethylene oxide at 30-35° C. over the course of about 2 hours. After 3 hours at 60° C., the reaction mixture was placed on 200 g of ice and adjusted to pH 1 with sulphuric acid. After triple extraction with in each case 50 ml of methylene chloride, the combined organic phases were extracted once by shaking with 30 ml of water, dried over magnesium sulphate and concentrated on a rotary evaporator. There remained an oil, in which, according to GC/MS analysis, the ratio of 2-(2,6-dimethylphenyl)ethanol to 1-(2,6-dimethylphenyl)ethanol was 81:19.

Use Example 1: 4-Chloro-2,6-dimethylphenylacetic acid

To a solution of 5 g of 2-(4-chloro-2,6-dimethylphenyl)ethanol (24 mmol, purity 90%) in 20 g of acetonitrile were added 38 mg of 2,2,6,6-tetramethylpiperidinyloxyl (0.24 mmol) at room temperature. To this solution were added, at 45° C., 0.8 ml of 11.05% strength sodium hypochlorite solution and then 4.3 g of sodium chlorite (36 mmol), dissolved in 12.5 g of a phosphate buffer (10.65 g of $Na_2HPO_4$ and 10.21 g of $KH_2PO_4$ per 1000 ml of water) were added dropwise over the course of one hour using a metering pump. When the addition was complete, the mixture was after-stirred for 30 min and cooled to 5-10° C. and 3 g of sodium sulphite were added in portions. The reaction mixture was then after-stirred for one hour and adjusted to pH 13.5 with 45% strength sodium hydroxide solution and the resulting suspension was extracted twice with in each case 25 ml of MTBE. The aqueous phase was adjusted to pH 3.38 with 10% strength hydrochloric acid and extracted three times with in each case 30 ml of MTBE. The combined organic phases of the acid extraction were dried and concentrated. This gave 4.3 g of product (87% of theory; purity 98% according to HPLC and quant. NMR).

The invention claimed is:
1. A process for preparing a compound of formula (I)

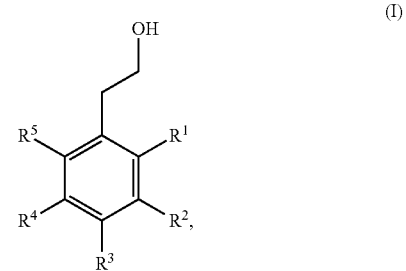

in which
$R^1$, $R^5$ independently of one another represent $C_1$-$C_6$-alkyl, $C_1$-$C_6$-fluoroalkyl having 1 to 13 fluorine atoms, optionally substituted $C_6$-$C_{10}$-aryl, fluorine, chlorine, a radical $NR^6_2$, $OR^6$ or $SR^6$, where
$R^6$ represents $C_1$-$C_6$-alkyl, $C_1$-$C_2$-fluoroalkyl having 1 to 5 fluorine atoms or phenyl,
$R^2$, $R^3$, $R^4$ independently of one another represent hydrogen, $C_1$-$C_6$-alkyl, $C_1$-$C_6$-fluoroalkyl having 1 to 13 fluorine atoms, optionally substituted $C_6$-$C_{10}$-aryl, fluorine, chlorine, a radical $NR^6_2$, $OR^6$ or $SR^6$, where
$R^6$ represents $C_1$-$C_6$-alkyl, $C_1$-$C_2$-fluoroalkyl having 1 to 5 fluorine atoms or phenyl, the process comprising reacting a compound of the formula (II)

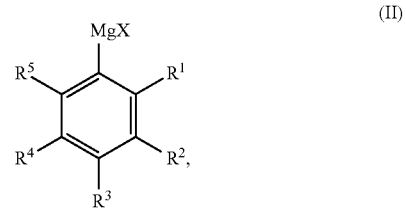

in which the radicals $R^1$ to $R^5$ have the meanings given above and
X represents chlorine, bromine or iodine,
in the presence of a copper compound with ethylene oxide,
wherein the compound of formula (I) is 2-(4-chloro-2,6-dimethylphenyl)ethanol.

2. The process for preparing a compound of formula (I) according to claim 1, wherein the copper compound used is copper(I) iodide, copper(I) bromide, copper(II) bromide or copper(I) chloride.

3. The process for preparing a compound of formula (I) according to claim 1, wherein the copper compound is used in an amount of from 0.1 to 50 mol percent, based on the compound of formula (II).

4. The process for preparing a compound of formula (I) according to claim 1, wherein the copper compound is used in an amount of from 0.5 to 15 mol percent, based on the compound of formula (II).

5. The process for preparing a compound of formula (I) according to claim 1, wherein ethylene oxide is used in an amount between 0.9 and 3 mol equivalents, based on the compound of formula (II).

6. The process for preparing a compound of formula (I) according to claim 1, wherein ethylene oxide is used in an amount between 1 and 2 mol equivalents, based on the compound of formula (II).

7. A compound of formula (I)

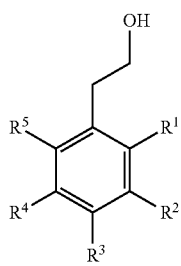

(I)

in which $R^1$, $R^2$, $R^3$, $R^4$, $R^5$ have the meanings given in the table

| $R^1$ | $R^2$ | $R^3$ | $R^4$ | $R^5$ |
|-------|-------|-------|-------|-------|
| Me    | H     | Cl    | H     | Me    |
| Me    | H     | Cl    | H     | Et    |
| Et    | H     | Cl    | H     | Et    |
| Me    | H     | Cl    | H     | n-Pr  |
| Et    | H     | Cl    | H     | n-Pr  |
| n-Pr  | H     | Cl    | H     | n-Pr  |
| Me    | H     | Cl    | H     | iso-Pr |
| Et    | H     | Cl    | H     | iso-Pr |
| iso-Pr | H    | Cl    | H     | iso-Pr |
| iso-Pr | H    | Cl    | H     | n-Pr  |
| Me    | H     | F     | H     | Me    |
| Me    | H     | F     | H     | Et    |
| Et    | H     | F     | H     | Et    |
| Me    | H     | $CF_3$ | H    | Me    |
| Me    | H     | $CF_3$ | H    | Et    |
| Et    | H     | $CF_3$ | H    | Et    |
| Me    | H     | $OCF_3$ | H   | Me    |
| Me    | H     | Me    | H     | Et    |
| Me    | H     | Et    | H     | Et    |
| Me    | H     | Et    | H     | Me    |
| Me    | Cl    | H     | H     | Me    |
| Et    | Cl    | H     | H     | Me    |
| Et    | H     | H     | Cl    | Me    | with the proviso that $R^3$ is selected from Cl, F, $CF_3$ or $OCF_3$ or with the proviso that $R^2$ or $R^4$ is Cl.

8. The compound of claim 7, wherein $R^3$ is selected from Cl, F, $CF_3$ or $OCF_3$.

9. The compound of claim 7, wherein $R^2$ or $R^4$ is Cl.

10. The compound of claim 7, which is 2-(4-chloro-2,6-dimethylphenyl)ethanol.

* * * * *